United States Patent
Chang et al.

(10) Patent No.: US 8,551,391 B2
(45) Date of Patent: *Oct. 8, 2013

(54) METHOD OF MAKING MICRONEEDLES

(75) Inventors: Eng-Pi Chang, Arcadia, CA (US); Philip Yi Zhi Chu, Monrovia, CA (US); Hsiao Ken Chuang, Arcadia, CA (US); Kejian (Kevin) Huang, Buffalo Grove, IL (US); Michael Lang, Chagrin Falls, OH (US); Reza Mehrabi, Tujunga, CA (US); Ronald F. Sieloff, Chardon, OH (US); Karen L. Spilizewski, Euclid, OH (US); Mark Wisniewski, Mentor, OH (US)

(73) Assignee: Avery Dennison Corporation, Pasadena, CA (US)

( * ) Notice: Subject to any disclaimer, the term of this patent is extended or adjusted under 35 U.S.C. 154(b) by 1841 days.

This patent is subject to a terminal disclaimer.

(21) Appl. No.: 11/050,116

(22) Filed: Feb. 3, 2005

(65) Prior Publication Data

US 2005/0178760 A1    Aug. 18, 2005

Related U.S. Application Data

(60) Provisional application No. 60/545,248, filed on Feb. 17, 2004.

(51) Int. Cl.
*H05B 1/02* (2006.01)

(52) U.S. Cl.
USPC ........ 264/481; 264/492; 264/297.8; 264/319; 425/407; 425/348 R

(58) Field of Classification Search
USPC .......... 264/409, 405, 402, 327, 337, 492, 264/297.8, 319, 481; 604/272; 425/407, 425/348 R See application file for complete search history.

(56) References Cited

U.S. PATENT DOCUMENTS

| | | | | |
|---|---|---|---|---|
| 2,135,763 | A | * | 11/1938 | Nicholson .................. 100/308 |
| 3,066,351 | A | * | 12/1962 | Schriner .................... 264/297.7 |
| 4,937,026 | A | | 6/1990 | Goossens et al. |
| 5,002,476 | A | * | 3/1991 | Kerr .......................... 425/174.4 |
| 5,063,112 | A | * | 11/1991 | Gross et al. ................. 428/412 |
| 5,078,947 | A | * | 1/1992 | Nishizawa et al. ........... 264/1.1 |
| 5,364,374 | A | | 11/1994 | Morrison et al. ............ 604/272 |

(Continued)

FOREIGN PATENT DOCUMENTS

| EP | 1 174 078 | 1/2002 |
|---|---|---|
| EP | 1 287 847 | 3/2003 |

(Continued)

OTHER PUBLICATIONS

PCT/US2005/003197; PCT International Search Report mailed May 19, 2005.

*Primary Examiner* — Christina Johnson
*Assistant Examiner* — Saeed Huda
(74) *Attorney, Agent, or Firm* — Avery Dennison Corporation

(57) ABSTRACT

A method of making a microneedle array structure (20) comprising a plurality of simultaneously formed microneedles (24), each microneedle (24) having a protrusion (32) and a passageway (34) extending therethrough. The method comprises the steps of pressing an embossable sheet material between a complimentary tools and radiantly heating the sheet material using radiant energy from a radiant energy source. One tool is relatively-radiantly-transparent, and another tool and/or the sheet material is relatively-radiantly-absorptive.

17 Claims, 11 Drawing Sheets

(56) References Cited

U.S. PATENT DOCUMENTS

| | | | |
|---|---|---|---|
| 5,381,753 A | 1/1995 | Okajima et al. | 117/12 |
| 5,453,100 A | 9/1995 | Sieloff | |
| 5,871,022 A | 2/1999 | Munoz et al. | 134/63 |
| 5,928,207 A | 7/1999 | Pisano et al. | 604/272 |
| 5,953,306 A | 9/1999 | Yi | 369/126 |
| 6,033,928 A | 3/2000 | Eriguchi et al. | 438/42 |
| 6,087,197 A | 7/2000 | Eriguchi et al. | 438/42 |
| 6,090,790 A | 7/2000 | Eriksson | 514/44 |
| 6,132,755 A * | 10/2000 | Eicher et al. | 424/427 |
| 6,177,291 B1 | 1/2001 | Eriguchi et al. | 438/42 |
| 6,193,898 B1 | 2/2001 | Kano et al. | |
| 6,312,612 B1 | 11/2001 | Sherman et al. | 216/2 |
| 6,334,856 B1 | 1/2002 | Allen et al. | 604/191 |
| 6,406,638 B1 | 6/2002 | Stoeber et al. | 216/11 |
| 6,440,096 B1 | 8/2002 | Lastovich et al. | 604/27 |
| 6,451,240 B1 | 9/2002 | Sherman et al. | 264/504 |
| 6,471,903 B2 | 10/2002 | Sherman et al. | 264/328.1 |
| 6,489,629 B1 | 12/2002 | Eriguchi et al. | 257/14 |
| 6,503,231 B1 | 1/2003 | Prausnitz et al. | 604/272 |
| 6,511,463 B1 | 1/2003 | Wood et al. | 604/272 |
| 6,533,949 B1 | 3/2003 | Yeshurun et al. | 216/11 |
| 6,547,803 B2 | 4/2003 | Seward et al. | 606/185 |
| 6,551,849 B1 | 4/2003 | Kenney | 438/34 |
| 6,565,532 B1 | 5/2003 | Yuzhakov et al. | 604/142 |
| 6,565,871 B2 | 5/2003 | Roser et al. | 424/423 |
| 6,583,350 B1 * | 6/2003 | Gee et al. | 136/253 |
| 7,416,692 B2 * | 8/2008 | Bharadwaj et al. | 264/446 |
| 2002/0006355 A1 | 1/2002 | Whitson | 422/56 |
| 2002/0020688 A1 * | 2/2002 | Sherman et al. | 216/2 |
| 2002/0082543 A1 | 6/2002 | Park et al. | 604/21 |
| 2002/0133129 A1 | 9/2002 | Arias et al. | 604/272 |
| 2002/0138049 A1 | 9/2002 | Allen et al. | 604/272 |
| 2002/0155737 A1 | 10/2002 | Roy et al. | 439/66 |
| 2002/0183688 A1 | 12/2002 | Lastovich et al. | 604/27 |
| 2002/0188310 A1 | 12/2002 | Seward et al. | 606/185 |
| 2002/0193818 A1 | 12/2002 | Sparks | 606/185 |
| 2003/0009113 A1 | 1/2003 | Olson | 600/573 |
| 2003/0045837 A1 | 3/2003 | Delmore et al. | 604/173 |
| 2003/0078549 A1 | 4/2003 | Stupar et al. | 604/272 |
| 2003/0081956 A1 * | 5/2003 | Stoebe et al. | 396/575 |
| 2003/0095582 A1 | 5/2003 | Ackley | 372/108 |
| 2003/0111759 A1 | 6/2003 | Wood et al. | 264/131 |
| 2003/0135161 A1 | 7/2003 | Fleming et al. | 604/173 |
| 2003/0135167 A1 | 7/2003 | Gonnelli | 604/272 |
| 2004/0142150 A1 * | 7/2004 | Bharadwaj et al. | 428/167 |

FOREIGN PATENT DOCUMENTS

| | | |
|---|---|---|
| WO | 99/47341 | 9/1999 |
| WO | 99/64580 | 12/1999 |
| WO | 00/74764 | 12/2000 |
| WO | 01/33614 | 5/2001 |
| WO | 01/36036 | 5/2001 |
| WO | 02/05890 | 1/2002 |
| WO | 02/15960 | 2/2002 |
| WO | 02/17985 | 3/2002 |
| WO | 02/43937 | 6/2002 |
| WO | 02/068189 | 9/2002 |
| WO | 02/072189 | 9/2002 |
| WO | 03/15860 | 2/2003 |
| WO | 03/020359 | 3/2003 |
| WO | 03/026733 | 4/2003 |

* cited by examiner

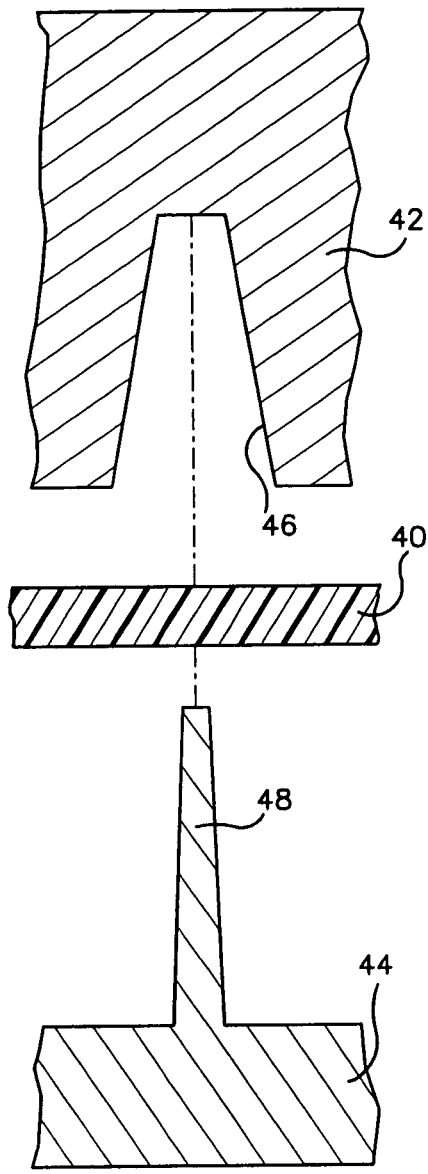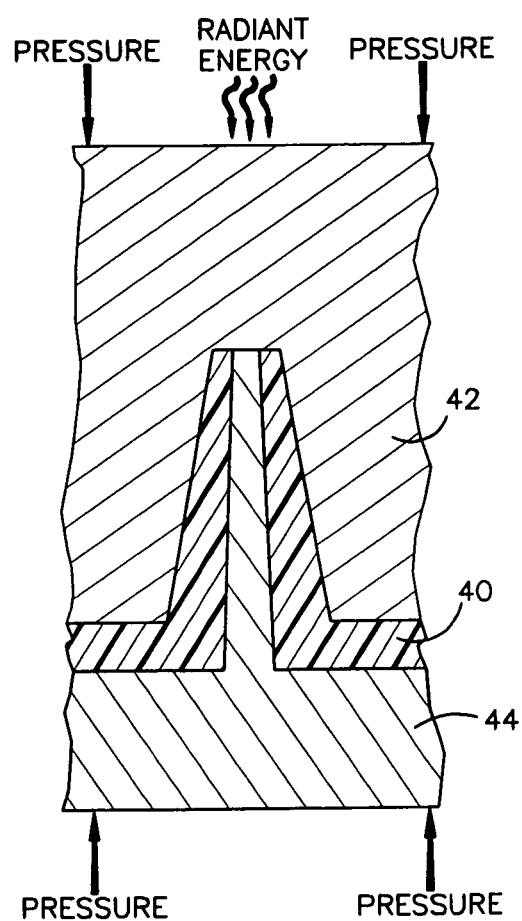
Figure 4A
Figure 4B

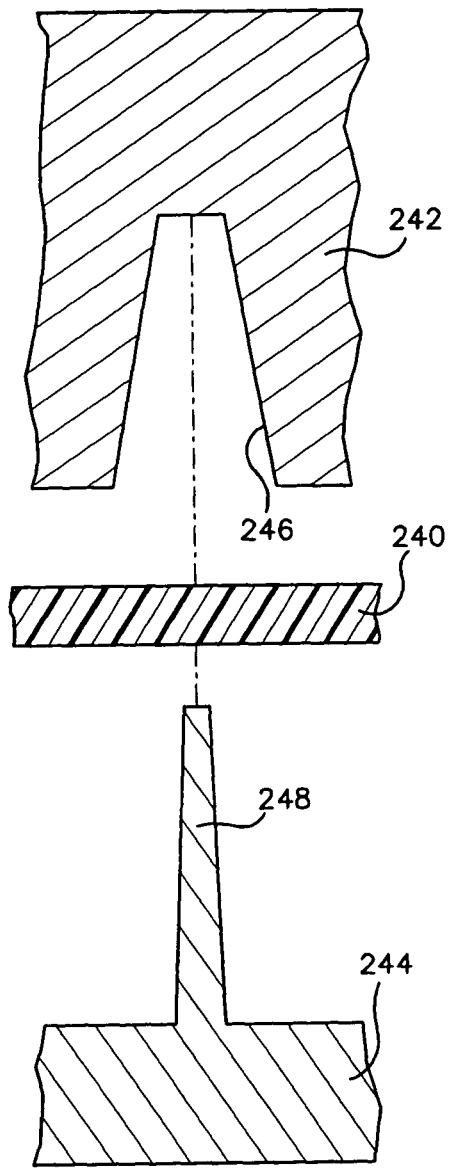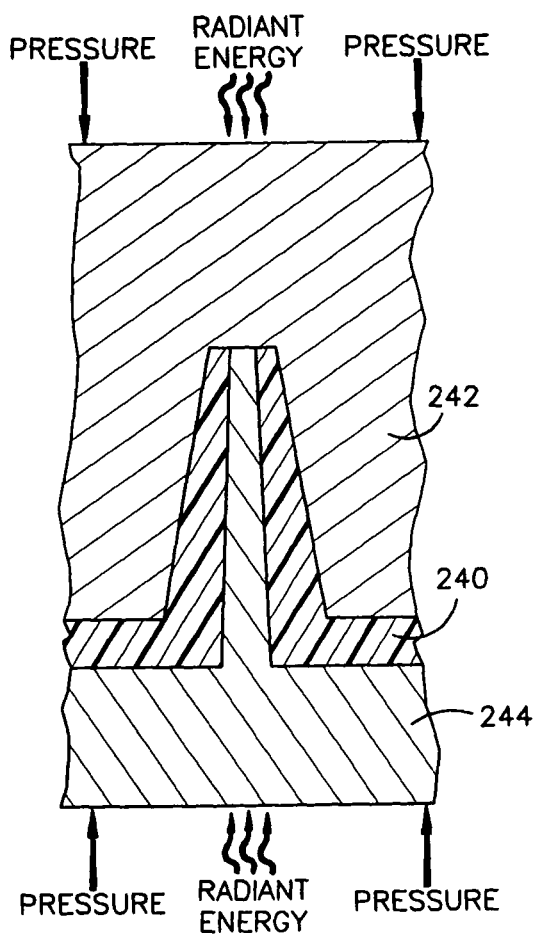
Figure 10A
Figure 10B

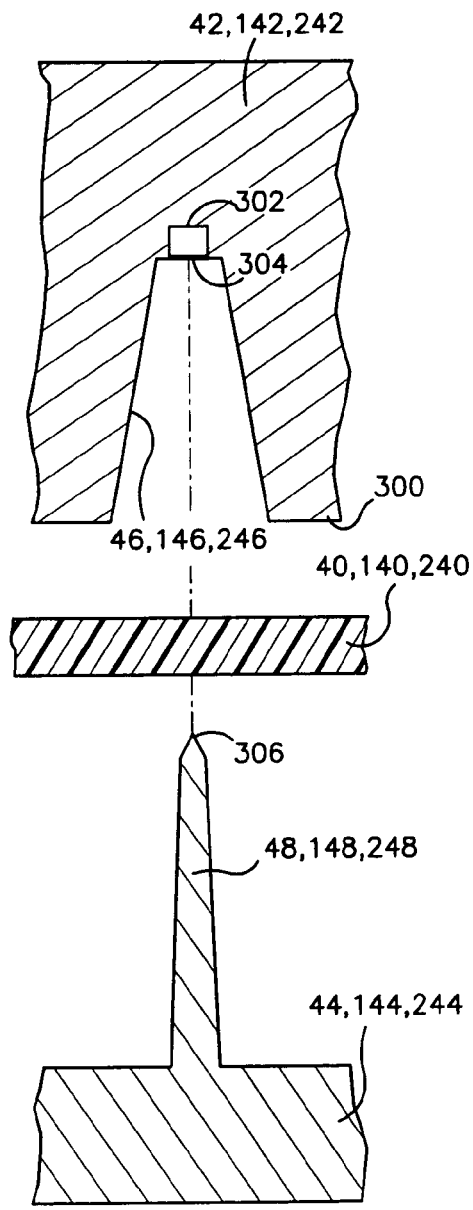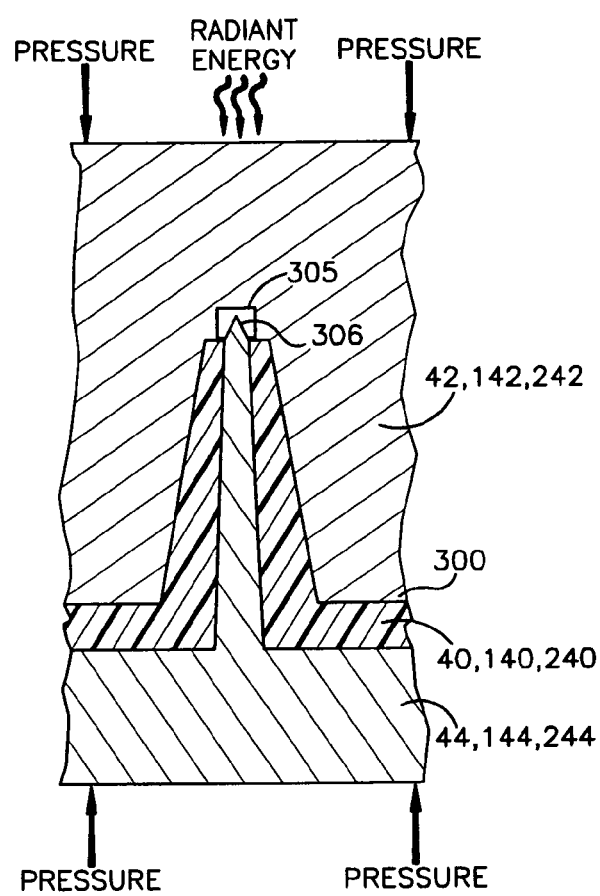
Figure 14A
Figure 14B

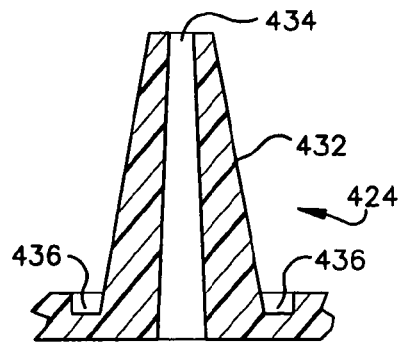
Figure 17
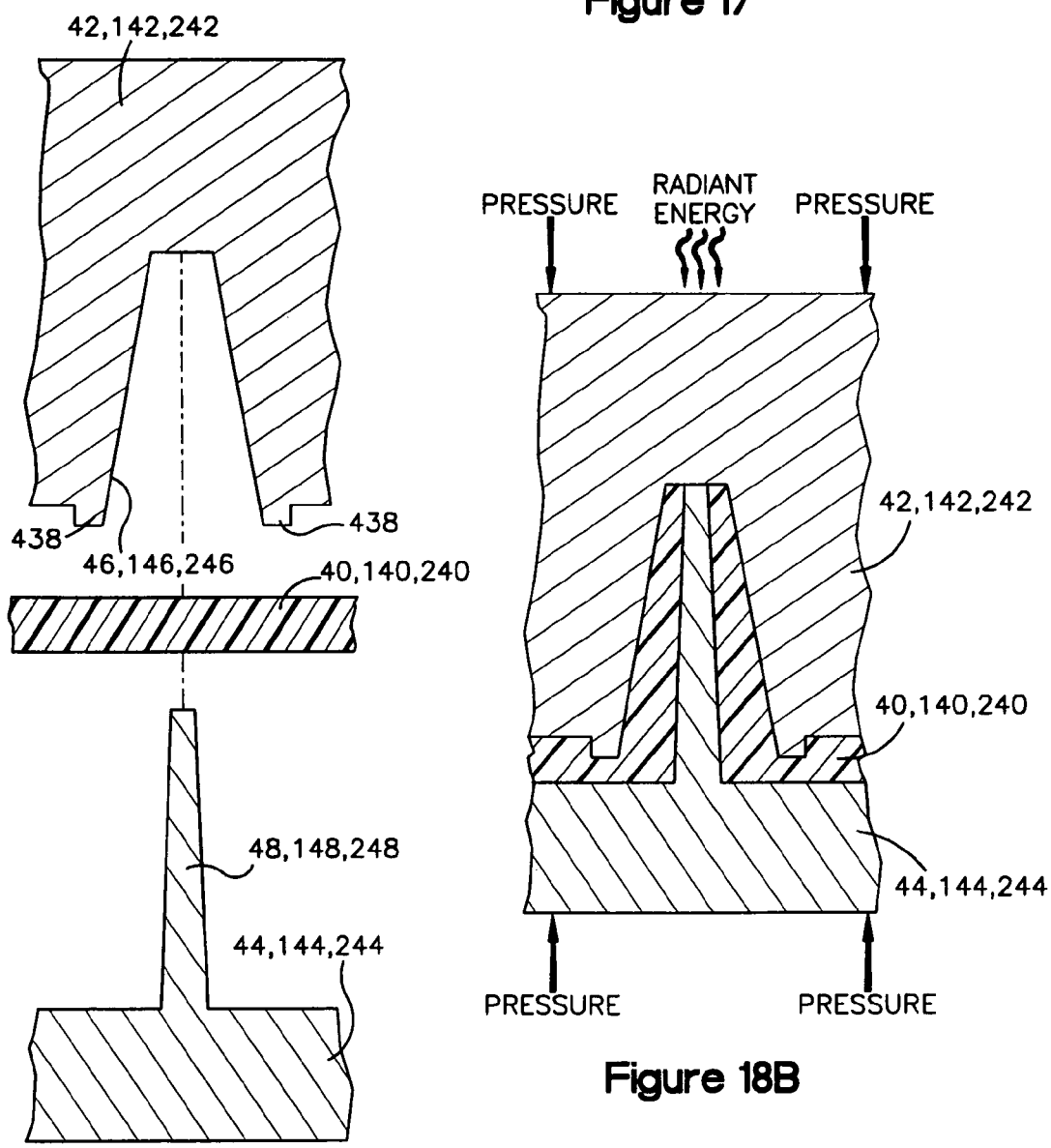
Figure 18A
Figure 18B

METHOD OF MAKING MICRONEEDLES

RELATED APPLICATION

This application claims priority under 35 U.S.C. §119(e) to U.S. Provisional Patent Application No. 60/545,248 filed on Feb. 17, 2004. The entire disclosure of this earlier application is hereby incorporated by reference.

FIELD OF THE INVENTION

This invention relates generally, as indicated, to a method of making microneedles and, more particularly, to a method of making hollow microneedles comprising a protrusion and a passageway extending therethrough.

BACKGROUND OF THE INVENTION

Topical delivery of drugs is a very useful method for achieving systemic or localized pharmacological effects. The use of microneedles has great advantages, in that intracutaneous drug delivery can be accomplished without pain and without bleeding. Of particular relevance to the present invention are hollow microneedles, which each comprise a protrusion and a passageway therethrough. The passageway allows fluids to pass from an internal chamber through the passageway and into a patient's skin or, alternatively, body fluid samples to pass from a patient through the passageway and into an internal chamber.

SUMMARY OF THE INVENTION

The present invention provides a method of making a microneedle wherein radiant energy is used as the sole or primary heat source, with the sheet material and tools being selectively relatively-radiantly-transparent or relatively-radiantly-absorptive, whichever will best perform the embossing process. Radiant energy heat transfer, when compared to conductive and convective heat transfer, can offer significant process improvements and end-product precision enhancements. For example, radiant energy heat transfer is capable of achieving significantly higher heat fluxes and embossing temperatures. Also, radiant energy heating can allow precise control of heat transfer to the to-be-embossed materials and other system elements. Furthermore, radiant energy heating can be incorporated into continuous and non-continuous embossing systems, with effective interaction of key subsystems and more readily adapted heat output to the requirements of a given system.

More particularly, the present invention provides a method of making a microneedle having a protrusion and a passageway extending therethrough. In this method, a first tool is provided which has a recess that defines the microneedle protrusion, and a second tool is provided which has a projection that defines the passageway. The method comprises the steps of pressing an embossable sheet material between the first tool and the second tool and radiantly heating the sheet material using radiant energy (preferably near-infrared radiant energy) from a radiant energy source. The pressing step can be performed by a press comprising a first press incorporating the first tool and a second press incorporating the second tool. Alternatively, the pressing step can be performed by a continuous system comprising a first belt incorporating the first tool and a second belt incorporating the second tool.

In one embodiment of the invention, the sheet material is relatively-radiantly-transparent, the first tool is relatively-radiantly-transparent, and the second tool is relatively-radiantly-absorptive. The radiant energy source is positioned so that radiant energy passes through the first tool (e.g., a source positioned above the tool) and through the sheet material and is absorbed by the second tool. The second tool is then heated by the absorbed radiant energy, thereby heating the sheet material to an appropriate embossing temperature.

In another embodiment of the invention, the sheet material is relatively-radiantly-absorptive and the first tool is relatively-radiantly-transparent. The radiant energy source is positioned so that radiant energy passes through the first tool (e.g., a source is positioned above the tool) so that it can be absorbed by the sheet material. The sheet material is thereby heated to an appropriate embossing temperature.

In another embodiment of the invention, the sheet material is relatively-radiantly-absorptive, the first tool is relatively-radiantly-transparent, and the second tool is relatively-radiantly-transparent. The radiant energy source is positioned so that radiant energy passes through both the first tool and the second tool (e.g., a source is positioned above the first tool, and another source is positioned below the second tool) so that it passes to the sheet material for absorption. The sheet material is thereby heated to an appropriate embossing temperature.

If the sheet material is relatively-radiantly-transparent, it can comprise a suitable thermoplastic having an acceptable transparency. If the sheet material is relatively-radiantly-absorptive, it can be doped with an additive that increases radiant absorptivity. The relatively-radiant-transparent tools can be made of a clear thermoplastic or thermoset polymer material, glass, or quartz. The relatively-radiant-absorptive tools can be made of nickel or nickel alloys.

These and other features of the invention are fully described and particularly pointed out in the claims. The following description and drawings set forth in detail certain illustrative embodiments of the invention, which are indicative of but a few of the various ways in which the principles of the invention may be employed.

DRAWINGS

FIGS. 4A and 4B are schematic illustrations of a method of making the microneedle array structure according to the present invention.

FIGS. 10A and 10B are schematic illustrations of another method of making the microneedle array structure according to the present invention.

FIGS. 14A and 14B are schematic illustrations of the methods shown in FIGS. 4, 7, and 10 with a modified version of the tools.

FIG. 17 is a close up cross-sectional view of another version of one of the microneedles according to the present invention.

FIGS. 18A and 18B are schematic illustrations of another method of making the microneedle array structure according to the present invention.

DETAILED DESCRIPTION

Figure 1:
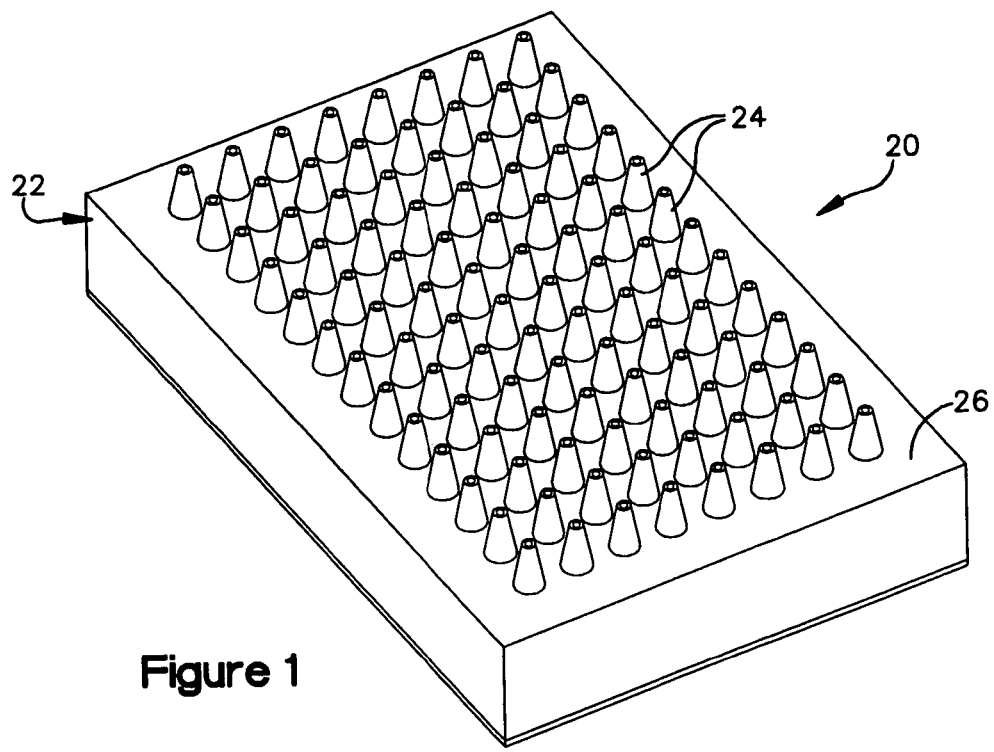
FIG. 1 is a perspective view of a microneedle array structure fabricated according to the method of the present invention.
Figure 2:
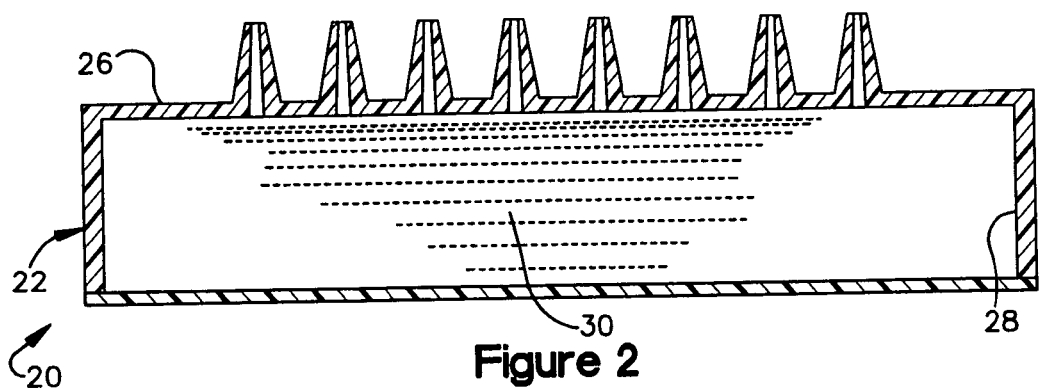
FIG. 2 is a cross-sectional view of the microneedle array structure.
Figure 3:
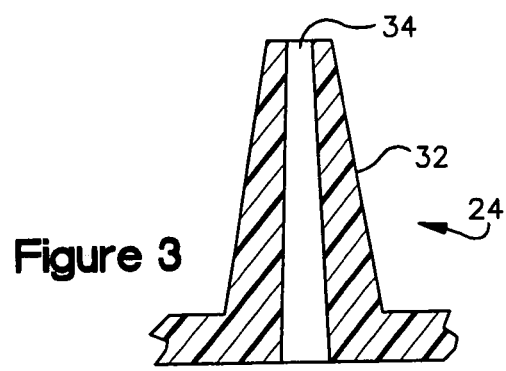
FIG. 3 is a close-up cross-sectional view of one of the microneedles in the array structure.

Referring now to the drawings, and initially to FIGS. 1-3, a microneedle array structure 20 according to the present invention is shown. The structure 20 comprises a substrate 22 and a plurality of microneedles 24. (FIG. 1.) The microneedles 24 can have, for example, a projection length ranging from about 1 μm to about 1 cm, having a cross-sectional dimension ranging from about 1 nm to about 1 mm, and having a pitch density ranging from about 1 μm to about 1 cm. In the illustrated embodiment, the substrate 22 comprises an exterior surface 26 from which the microneedles 24 outwardly extend and an interior surface 28 defining an internal chamber 30. (FIG. 2.) Each of the microneedles 24 comprises a protrusion 32 and a passageway 34 extending therethrough, with the passageway 34 being centrally located and extending through the tip of the protrusion 32.

Referring now to FIGS. 4A and 4B, a method of making the microneedle array structure 20 according to the present invention is schematically shown. In this method, a sheet material 40 is embossed by the mating of a first tool 42 and a second tool 44 and the subsequent application of radiant energy. The first tool 42 has a recess 46 corresponding to the microneedle protrusion 32, and the second tool 44 has a projection 48 corresponding to the passageway 34. The sheet material 40 and the first tool 42 are relatively-radiantly-transparent, and the second tool 44 is relatively-radiantly-absorbent. During the embossing process, the radiant energy passes through the first tool 42, through the sheet material 40, and to the second tool 44, whereat it is absorbed. The surface of the second tool 44 is thereby heated, which in turn heats the sheet material 40 to a suitable embossing temperature.

Figure 5:
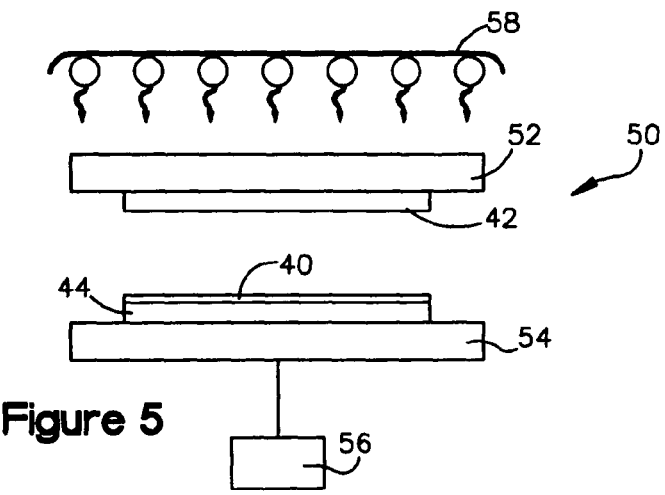
FIG. 5 is a schematic side view of a system for practicing the method of FIG. 4.

Referring now FIG. 5, a system 50 for making the microneedle array structure 20 according to the method shown in FIG. 4 is schematically shown. The system 50 is a press which comprises an upper press 52, a lower press 54, and a pressure-producing device 56 (e.g., an air cylinder). The upper press 52 incorporates the relatively-radiantly-transparent first tool 42, and the lower press 54 incorporates the relatively-radiantly-absorbent second tool 44. (It may be noted that the lower press 54 can include, for example, a press platform and a platen for placement thereon.) A source of radiant energy 58 (e.g., a heater) is positioned above the upper press 52 and may be movable so that it can be raised and lowered relative to the rest of the system.

In operation, the sheet material 40 is arranged on the lower press 54, and the pressure-producing device 56 is then used to press the lower press 54 against the upper press 52. The heater 58 is activated for a set period of time (e.g., in the order of seconds) to emboss the sheet material 40. The sheet material 40 is then cooled (e.g., by blowing cool air thereover), the pressure is removed (and the presses 52 and 54 separated), and the embossed sheet material can be removed.

Figure 6:
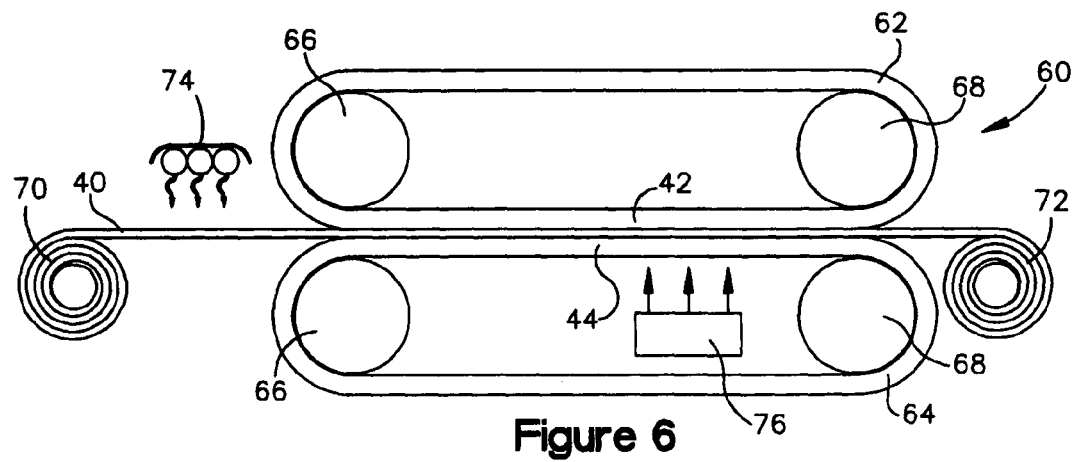
FIG. 6 is a schematic side view of another system for practicing the method of FIG. 4.

Referring now to FIG. 6, another embossing system 60 according to the present invention is schematically shown. The system 60 comprises an upper belt 62, a lower belt 64, upstream pressure rollers 66, downstream pressure rollers 68, a supply roll 70, and an uptake roll 72. The upper belt 62 incorporates the transparent first tool 42, and the lower belt 64 incorporates the absorptive second tool 44. A source of radiant heat 74 (e.g., a heater) is positioned above the sheet-contacting region of the upper belt 62, and a cooling station 76 is positioned downstream of the radiant heater 74. In operation, the sheet material 40 is conveyed from the supply roll 70 through the belts 62 and 64, and the rollers 66 and 68 maintain pressure against the belts and thus against the sheet material 40. In an upstream region, radiant heat passes through the upper belt 62 and the sheet material 40 to the lower belt 64 to emboss the sheet material. In a downstream region, the sheet material 40 is cooled by the cooling station 76 and is conveyed to the uptake roll 72.

Figure 7A:
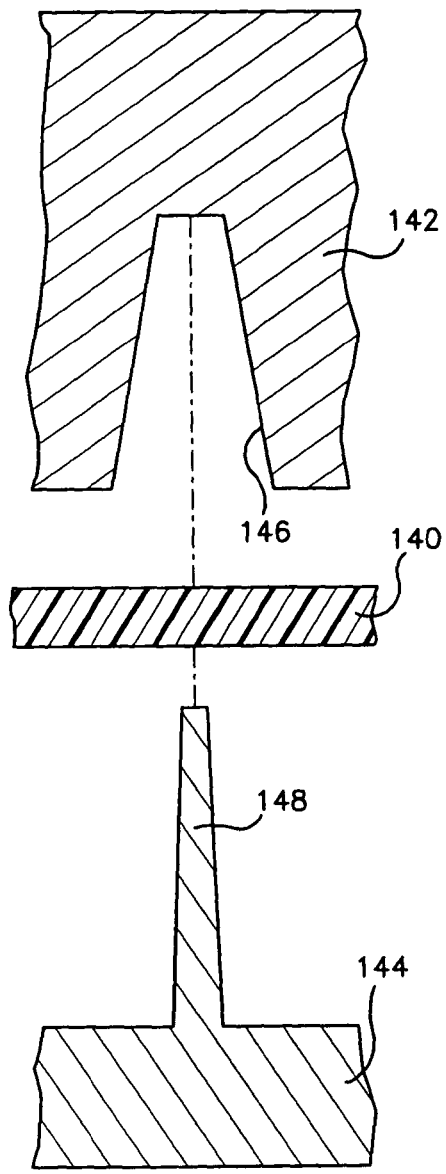
FIGS. 7A and 7B are schematic illustrations of another method of making the microneedle array structure according to the present invention.
Figure 7B:
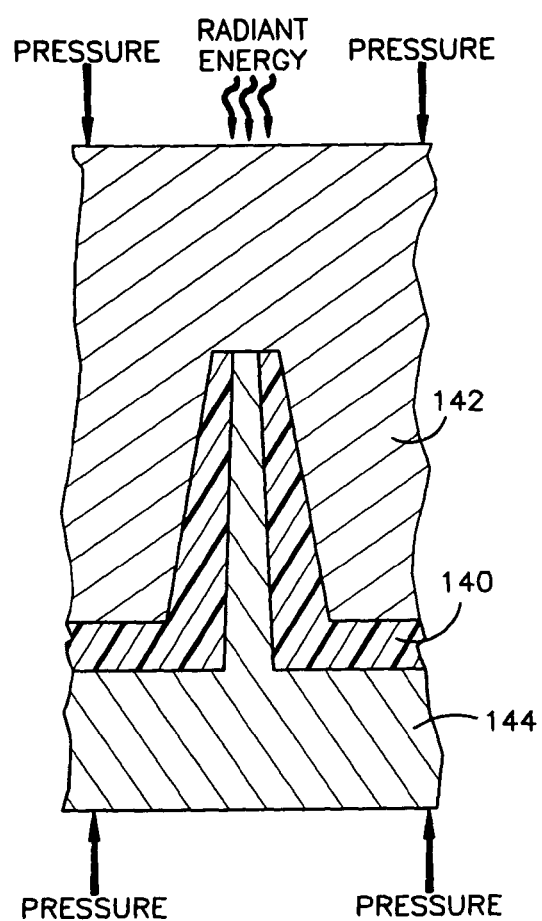

Referring now to FIGS. 7A and 7B, another method of making the microneedle array structure 20 according to the present invention is schematically shown. This method includes a sheet material 140, a first tool 142 (with a recess 146), and a second tool 144 (with a projection 148). In this method, the first tool 142 is transparent to radiant energy, and the sheet material 140 is absorptive of radiant energy. (The second tool 144 can be, but need not necessarily be, absorptive of radiant energy.) During the embossing process, the radiant energy passes through the transparent first tool 142 to the absorptive sheet material 140, which becomes soft and conforms to the hollow microneedle shape prescribed by the two mating tools 142 and 144.

Figure 8:
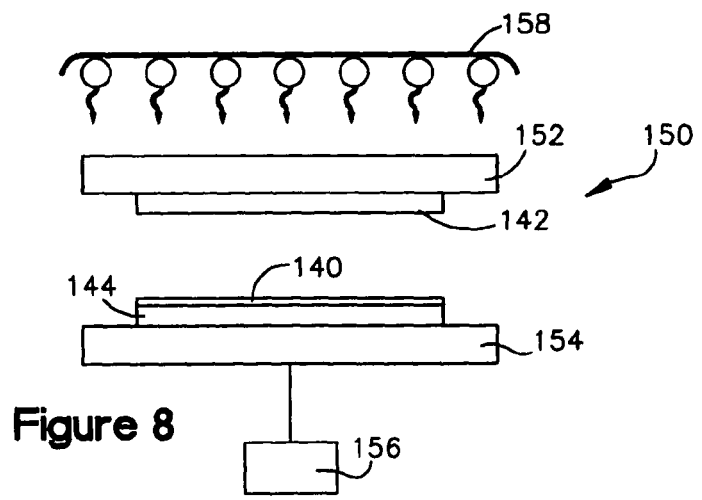
FIG. 8 is a schematic side view of a system for practicing the method of FIG. 7.
Figure 9:
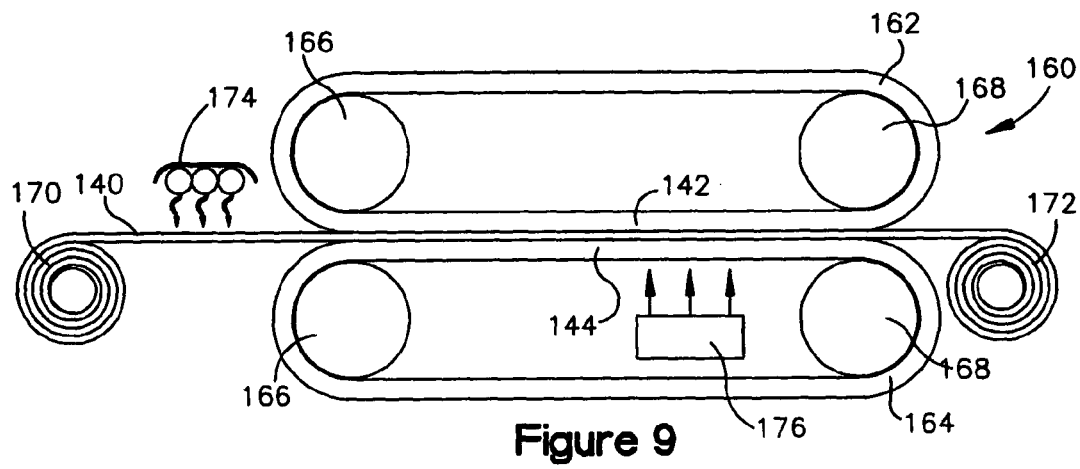
FIG. 9 is a schematic side view of another system for practicing the method of FIG. 7.

Referring now to FIGS. 8 and 9, systems 150 and 160, respectively, are shown for making the microneedle array structure 20 according to the method shown in FIG. 7. These systems 150/160 are similar to the systems 50/60 shown above, whereby like reference numerals are used to designate like parts, with a one hundred being added thereto. In fact, the same equipment could be used, with the relatively-radiantly-transparent sheet material 40 being replaced with the relatively-radiantly-absorptive sheet material 140.

Referring now to FIGS. 10A and 10B, another method of making the microneedle array structure 20 according to the present invention is schematically shown. This method includes a sheet material 240, a first tool 242 (with a recess 246), and a second tool 244 (with a projection 248). In this method, both the first tool 242 and the second tool 244 are transparent to radiant energy, and the sheet material 240 is absorptive of radiant energy. During the embossing process, the radiant energy passes through the transparent first tool 242 and the transparent second tool 244 to the absorptive sheet material 240, which becomes soft and conforms to the hollow microneedle shape prescribed by the two mating tools 242 and 244.

Figure 11:
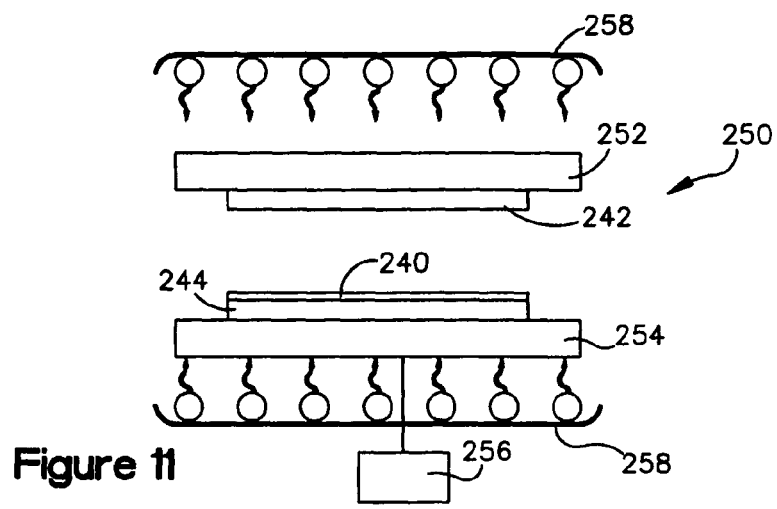
FIG. 11 is a schematic side view of a system for practicing the method of FIG. 10.
Figure 12:
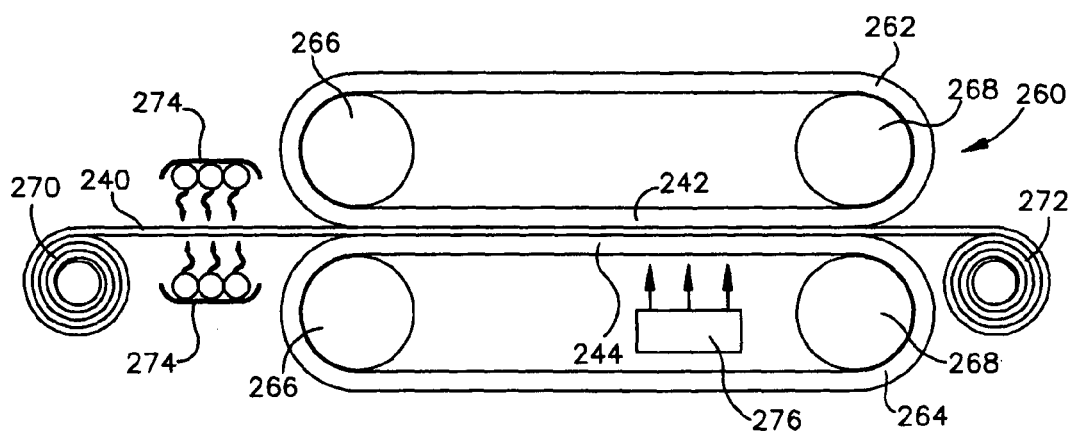
FIG. 12 is a schematic side view of another system for practicing the method of FIG. 10.

Referring now to FIGS. 11 and 12, systems 250 and 260, respectively, are shown for making the microneedle array structure 20 according to the method shown in FIG. 10. These systems 250/260 are similar to the systems 50/150 and 60/160 shown above, whereby like reference numerals are used to designate like parts, with a two hundred suffix. In the system 250, both the upper and lower presses 252 and 254 are relatively-radiantly-transparent, and heaters 258 are provided both above the upper press 252 and below the lower press 254. In the system 260, both the upper and lower belts 262 and 264 are relatively-radiantly-transparent and radiant heaters 274 are positioned both above an upstream sheet-contacting region of the upper belt 262 and below a downstream sheet-contacting region of the lower belt 264.

Figures 13A, 13B:
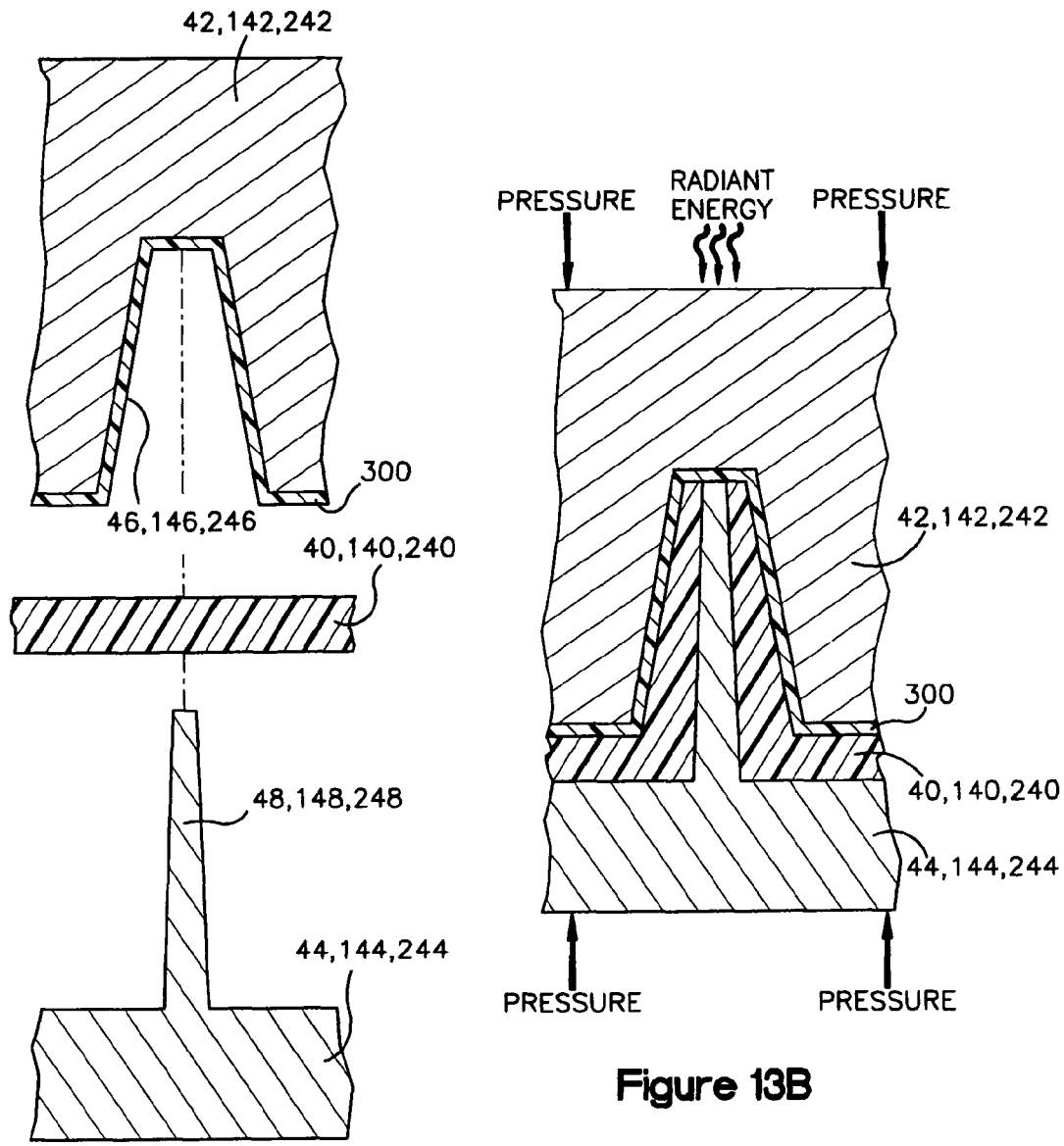
FIGS. 13A and 13B are schematic illustrations of the methods shown in FIGS. 4, 7, and 10 with a backing film being used.

Referring now to FIGS. 13A and 13B, a backing film 300 (e.g., a polymeric film) may be placed between the first tool 42/142/242 and the sheet material 40/140/240 in any of the above-methods. The backing film 300 serves as a cushion into which the projection 48/148/248 penetrates so as to ensure complete extension of the passageway 34 through the protrusion 32. The backing film 300 can be relatively-radiantly-transparent so as to not interfere with the transmission of the radiant energy through or to the sheet material 40/140/240. The backing film 300 could be peeled off after completion of embossing or could remain on the structure 20 for removal just prior to use.

Referring now FIGS. 14A and 14B, a modified version of the recess 46/146/246 and the projection 48/148/248 is shown which may be used with any of the above-described methods. Specifically, the end wall of the recess 46/146/246 may be provided with an indentation 302 which extends beyond the protrusion-defining profile. The indentation 302 is temporarily covered with a seal 304, which is punctured by a tip 306 of the projection 48/148/248 during mating of the tools 42/142/242 and 44/144/244 so as to ensure the complete extension of the passageway 34 through the microneedle protrusion 32.

Figure 15:
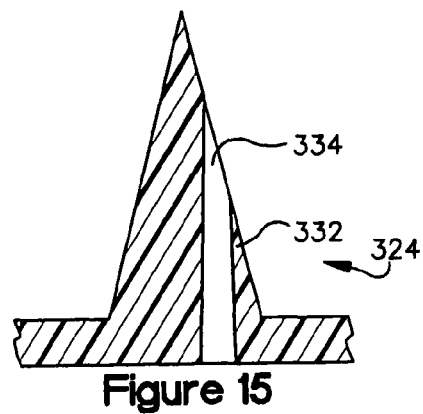
FIG. 15 is a close-up cross-sectional view of a modified version of one of the microneedles in the array structure.
Figure 16A:
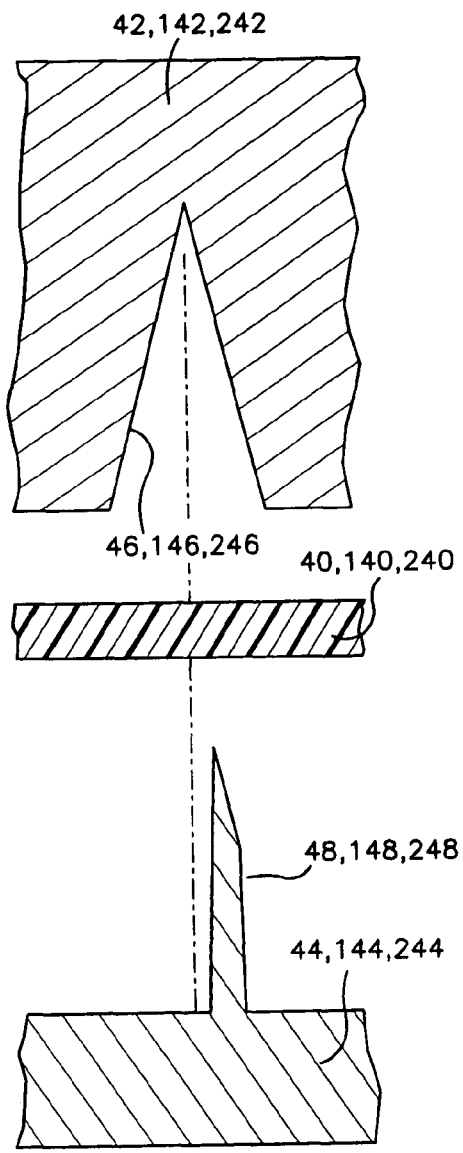
FIGS. 16A and 16B are schematic illustrations of a method of making the microneedle array structure according to the present invention.
Figure 16B:
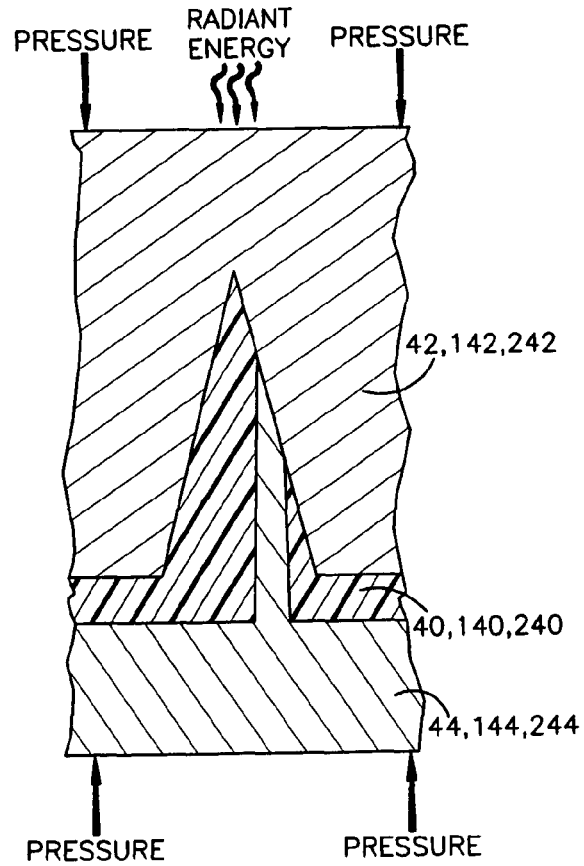

Referring now to FIG. 15, another microneedle 324 according to the present invention is shown. The microneedle 324, similar to the microneedle 24, comprises a protrusion 332 and a passageway 334 extending therethrough. The passageway 334, however, is not centrally located and/or does not extend through the tip of the protrusion 332. Instead, the passageway 334 extends through the side of the protrusion 332. This construction may be advantageous when a sharp end of the protrusion is desired for puncturing or other purposes and can be accomplished with a variety of other passageway geometries. As shown in FIGS. 16A and 16B, the microneedle 324 may be made in the same manner as the microneedle 24, with a first tool 42/142/242 and a second tool 44/144/244. Also, although not specifically shown in the drawings, the modifications shown in FIGS. 13 and 14 can also be used to make the microneedle 324.

Referring now to FIG. 17, another microneedle 424 according to the present invention is shown. The microneedle 424, similar to the microneedle 24, comprises a protrusion 432 and a passageway 434 extending therethrough. The microneedle 424 also includes an indent or recess 436 surrounding the protrusion 432. As shown in FIGS. 18A and 18B, the microneedle 424 may be made in the same manner as the microneedle 24, with a first tool 42/142/242 and a second tool 44/144/244, except that the second tool 44/144/244 also includes projections 438 for forming the recess 436. Also, although not specifically shown in the drawings, the modifications shown in FIGS. 13 and 14 can also be used to make the microneedle 324.

The methods and systems described above use radiant energy as the sole or primary heat source in carrying out a heat-plus-pressure embossing process. Radiant energy heat transfer, in comparison to conductive and convective heat transfer, is capable of achieving significantly higher heat fluxes and embossing temperatures.

Radiant energy heating offers various means to precisely control heat transfer to materials to be embossed and other elements of the method/system that cannot be achieved through conductive and convective heating. Specifically, for example, control of the thermal radiation source by reflection, focusing, filtering, etc. can be employed to regulate the spectral and geometric distribution of the radiation. Additionally or alternatively, controlled radiant heat transfer can be accomplished by designing the to-be-embossed sheet material through doping or multilayer structures so as to regulate absorption of the thermal radiation. Controlled radiant heating can translate into other process improvements, such as reduction of cooling requirements and/or improved embossing precision via coordination between localized heat and pressure during embossing.

Radiant energy heating can be incorporated into continuous and non-continuous embossing systems, which demonstrate effective interaction of key subsystems (e.g., radiant heat source optics, embossing tooling, pressurizing structures, webstock-handling mechanisms, etc.).

Numerical simulations indicate significant and qualitative differences between radiation and other heating methods (e.g. purely conductive heating). For example, the surface temperature of a sheet material (film) will rise sharply in a conductive process, versus a smooth rise for NIR or other radiative heating. For this and other reasons, radiant heating more readily adapts heat output to the requirements of a given system than does conductive heating. Higher temperatures are made possible just by increasing the duration of radiant heating. Also, it is possible to change the temperature by changing the thickness of the tool (i.e. its thermal mass).

The sheet material 40/140/240 and the tools 42/142/242 and 44/144/244 have been described above as being either a relatively-radiantly-transparent material or a relatively-radiantly-absorptive material. A relatively-radiantly-transparent material (also referred to a "relatively-transparent material" or a "transparent material") can be defined as a solid material that is less absorptive of the radiant energy than a relatively-radiantly-absorptive material (also referred to as a "relatively-absorptive material" or an "absorptive material").

This definition requires a comparison of materials, in that a material is only transparent or absorptive relative to another material. Furthermore, a material may be relatively transparent in one device or system, and relatively absorptive in another. The concept of relativity that is employed in this definition is that involving specific absorptive properties of a material and its absorptivity per unit volume or per unit mass. Additionally, the definition is tied to the spectral emissivity distribution of radiant energy employed. A material may be relatively absorptive with regard to another material with respect to a first source of radiant energy, and may also be relatively transparent with regard to the same material with respect to a second radiant energy of a different spectral emissivity distribution.

It should be noted that even a relatively transparent material may have some level of absorptivity of the radiant energy. Thus, while the radiant energy may be described here as passing through the transparent material and as heating only the absorptive material, it will be appreciated that some absorption into and heating of the transparent material may in fact occur.

The relatively-transparent and the relatively-absorptive materials can be characterized more narrowly based upon a relative ratio of their absorptivity (e.g., the relatively-absorptive material having an absorptivity that is at least seven times that of the relatively-transparent material). The materials can be characterized by comparing their total rate of energy absorption (total energy absorbed per time) with, for example, the ratio of energy absorbed by the relatively-transparent material to the ratio of energy absorbed by the relatively-absorptive material being less than 1, being less than or equal to 0.7, being less than or equal to 0.5, being less than or equal to 0.3, being less than or equal to 0.1, or being nearly zero.

The relatively-radiant-transparent sheet material 40 can comprise various thermoplastic polymeric sheeting or films which are nearly transparent to the emitted energy (i.e., they do not absorb very much below about 2 microns wavelength). The sheet material may combine such a film or sheeting with a carrier film, e.g. Mylar®, which likewise is highly transparent to the radiant energy. The film 300 (FIG. 13) can be made of similar materials.

The sheet material 40 has two significant temperature reference points, namely $T_g$, the glass transition temperature (at which plastic material will change from the glassy state to the rubbery state), and $T_e$, the embossing temperature. At the embossing temperature $T_e$, the material flows enough to be permanently deformed and will, upon cooling, retain a form and shape that matches or has a controlled variation (e.g. with shrinkage) of the embossing tool. Because $T_e$ will vary from material to material and also will depend on the thickness of the film material and the nature of the dynamics of press system being used, the exact $T_e$ temperature is related to process conditions including the embossing pressure(s), the temperature input of the continuous press and the press speed, as well as the extent of both the heating and cooling sections in the reaction zone. In any event, the embossing temperature $T_e$ must be high enough to exceed the glass transition temperature $T_g$ so that adequate flow of the material can be achieved so as to provide highly accurate embossing of the film. If the film 300 (FIG. 13) is used, it can be selected to have a glass transition temperature $T_g$ greater than that of the sheet material 40/140/240.

Numerous thermoplastic materials can be considered as candidates for the sheet material 40. Suitable materials include thermoplastics of a relatively low glass transition temperature (up to 302° F./150° C.), as well as materials of a higher glass transition temperature (above 302° F./150° C.). Typical lower glass transition temperature thermoplastic materials (i.e. with glass transition temperatures up to 302° F./150° C.) include vinyl, polymethyl methyacrylate, low $T_g$ polycarbonate, polyurethane, and acrylonitrile butadiene styrene (ABS). The glass transition $T_g$ temperatures for such materials are 158° F., 212° F., 302° F., and 140° to 212° F. (70° C., 100° C., 150° C., and 60° to 100° C.). Higher glass transition temperature thermoplastic materials (i.e. with glass transition temperatures above 302° F./150° C.) include polysulfone, polyacrylate, cyclo-olefinic copolymer, high $T_g$ polycarbonate, and polyether imide.

A table of exemplary thermoplastic materials, and their glass transition temperatures, appears below as Table I:

TABLE I

| Symbol | Polymer Chemical Name | $T_g$ ° C. | $T_g$ ° F. |
|---|---|---|---|
| PVC | Polyvinyl Chloride | 70 | 158 |
| Phenoxy | Poly (Hydroxyether) | 95 | 403 |
| PMMA | Polymethyl methacrylate | 100 | 212 |
| BPA-PC | Bisphenol-A Polycarbonate | 150 | 302 |
| COC | Cyclo-olefinic copolymer | 163 | 325 |
| PSF | Polysulfone | 190 | 374 |
| Polyacrylate | Polyacrylate | 210 | 410 |
| Hi-$T_g$-PC | High $T_g$ polycarbonate | 260 | 500 |
| PEI | Polyether imide | 215 | 500 |
| Polyurethane | Polyurethane | varies | varies |
| ABS | Acrylonitrile Butadiene Styrene | 60-100 | 140-212 |

The relatively-radiantly-absorbent sheet materials 140 and 240 can be achieved by the inclusion of suitable dopants in the sheet material. The term dopant, as used herein, is a relatively-radiantly-absorbent material which is in or on the sheet material 140/240. Thus, a dopant may be actually within the polymer or other material or component of the sheet material 140/240. Additionally or alternatively, the dopant may be a coating on the sheet material 140/240. Such dopants may be dispersed throughout the sheet material 140/240; may be chemically reacted throughout part or all of the sheet material 140/240; and/or may be in a separate phase on or within the sheet material 140/240.

The desirable concentration of the dopant in the plastic may depend on the type of polymer material and the wavelength and energy of the radiant energy employed, among other factors. (A small proportion of dopant may not substantially alter the material properties of the polymer sheet material, and hence may have little or no effect on its processability.) Examples of suitable dopants are Epolight 1125, 1178, and 3063 near-infrared absorbing dyes available from Epolin, Inc., of Newark, N.J.

Incorporation of a dopant within the thermoplastic can take place by mixing the plastic pellets with the dopant, followed by shaping with exposure to heat. Other conventional mixing techniques, including compound extrusion, would be known to one of ordinary skill in the art. During incorporation of the dopant, the plastic pellets may, if desired, be treated with adhesion promoters, polymer-compatible solvents, stabilizers and/or surfactants resistant to the operating temperatures used. The doped plastic pellets may be produced by placing the plastic pellets in a suitable mixer, wetting these with any additives, and then adding and incorporating the dopant. The resultant mixture may then be directly processed in an extruder.

Extruded films may have a homogeneous dopant distribution. On the other hand, a non-uniform distribution of the dopant may be desired in order to localize the radiant heating effect within a certain region of the polymeric substrate. One way this can be achieved is by including dopant within one layer of a multilayer coextrudate. Such localization, or non-uniform distribution of the dopant, can be achieved by strata or layers across the thickness dimension of the substrate. Localization of dopant also may be achieved within the plane of the substrate, e.g., by depositing or printing the dopant in a desired pattern, such as a grid. The dopant may comprise particulate matter, and also may comprise a coating. The coating may be a surface coating, or may be an interfacial coating or layer between layers of a multilayer substrate.

As a further alternative, the dopant may be impregnated into the sheet material 140/240. The sheet material 140/240 may be impregnated by swelling a surface of the sheet material 140/240 with a solvent, allowing the dopant to migrate into the swollen structure, and then removing the solvent, causing the swelling to reverse and trapping the dopant within a polymer structure of the sheet material 140/240. Further details regarding impregnation methods may be found in U.S. Pat. Nos. 4,937,026 and 5,453,100, which are herein incorporated by reference in their entireties.

The dopant may be placed in a pattern on or within the sheet material 140/240. For example, the dopant may be placed at locations within the sheet material 140/240 where deformation of the material is to be greatest.

The relatively-radiantly-transparent tools 42/142/242 and 44/144/244 can be fabricated from a clear thermoplastic or thermoset polymer material, glass, or quartz. If the first tool 42/142/242 is made from hard material, such as glass or quartz, the backing film 300 can be used. The relativelyradiantly-absorbtive tools 44 and 144 can be fabricated from nickel and/or nickel alloys, which are highly absorptive of NIR radiation. (Incident NIR radiation can rapidly heat nickel tooling to temperatures well above the 500° F. upper limit achieved by conventional circulatory oil heating of embossing tooling.) Clearly, the tools must have a higher glass transition temperature $T_g$ or a higher melting temperature $T_m$ than the sheet material 40/140/240.

The radiant heaters 58/158/258 and 74/174/274 can be high energy near infrared radiant (NIR) heating systems that use radiation operating at or above 4000K, and preferably at or above 3000K. The energy outputs of these emitters are several orders of magnitude larger than those of short-wave and medium-wave infrared emitters, and can provide high heat fluxes critical for effective heat-plus-pressure precision embossing. A preferred line of commercially available high-energy NIR systems is supplied by AdPhos AG, Bruckmühl-Heufeld, Germany (AdPhos). AdPhos infrared heating systems provide durable, high energy heating systems, and an AdPhos lamp acts as a blackbody emitter operating at about 3400K. Other radiant heaters and emitters that provide suitable thermal energy are available from various major lamp manufacturers (including Phillips, Ushio, General Electric, Sylvania, and Glenro). For example, these manufacturers produce emitters for epitaxial reactors used by the semiconductor industry. All of these emitters have temperatures over 3000 K. More broadly, however, suitable NIR sources may be emitters with temperatures over about 4000 K.

The output of a radiant energy source can be controlled in various ways to improve system performance. Most notably, through the use of reflectors (such as curved reflectors (parabolic or elliptic) at the rear of the lamp, and side reflectors), the useful radiant energy output can be significantly increased. Where it is desired to focus the thermal radiation on a very limited geometric area, this can be achieved through focusing optics and reflectors. Another technique is to selectively mask the radiant energy. It is also possible to change the spectral distribution of the emitted energy through filtering.

The cooling stations 76/176/276 may be any of a variety of suitable systems for cooling the sheet material 40/140/240 sufficiently so to allow it to retain the embossed pattern after the sheet material is separated from the tools 42/142/242 and 44/144/244. It may be noted that, in view of the localized heating possible with the present invention, cooling cycles may be speeded up and may use less energy. In a conventional embossing system using electrical or oil heating, a large machine (e.g., a heating drum) is heated and pressed against the material to be embossed. The large mass of the heated machine makes cooling of the embossed material more difficult, causing additional time and/or energy to be expended in order to accomplish the desired cooling. In fact, in order to practically effect cooling in such systems, separation of the embossed material from the heated machinery may be required, which may adversely affect the quality of the embossed product.

The embossing pressure is expected to be in the range of approximately 150 to 700 psi (1.03 to 4.82 MPa), and could be potentially higher. The appropriate pressure range will depend upon factors such as the operational range of the machinery, the mechanical strength of the embossing belt or tool (high pressure capacity), and the thermoplastic material and thickness of the thermoplastic film.

The tools can comprise suitable mechanical and/or electro-optical registration components in order to insure precise alignment. (It may be noted that the use of transparent constructions in radiative heating and embossing also lends itself to easy incorporation into optical registration devices.) Moreover, with the present invention, the tools 42/142/242 and 44/144/244 can be aligned once during the initial set-up of the process so that the tools remain in registration throughout the embossing run.

One may now appreciate that the present invention provides a method of making a microstructure wherein radiant energy is used as the sole or primary heat source, with the sheet material and tools being selectively relatively-radiantly-transparent or relatively-radiantly-absorptive, whichever will best perform the embossing process. Although the invention has been shown and described with respect to certain preferred embodiments, it is evident that equivalent and obvious alterations and modifications will occur to others skilled in the art upon the reading and understanding of this specification. For example, while in the embodiments described above the method concentrated on the making of microneedles, the present invention may find application in other microstructures having passageways extending therethrough. The present invention includes all such alterations and modifications and is limited only by the scope of the following claims.

The invention claimed is:

1. A method of making a microneedle having a protrusion and passageway extending therethrough, said method comprising the steps of:
    pressing an embossable, sheet material that is one of radiantly transparent or radiantly absorptive between a first radiant transparent tool having a recess which defines the protrusion and a second tool having a projection which defines the passageway;
    wherein the second tool can be radiantly-transparent or radiantly-absorptive; and
    radiantly heating the sheet material by using radiant energy from a vertically movable radiant energy source disposed above the first tool and below the second tool;
    wherein the first tool is radiantly-transparent and the radiant energy passes there through to the sheet material; and
    wherein at least one of the sheet material and the second tool is radiantly-absorptive.

2. A method as set forth in claim 1, wherein the radiant energy source supplies near-infrared energy.

3. A method as set forth in claim 1, wherein the radiant energy source includes a blackbody emitter having a temperature of at least 2000 K.

4. A method as set forth in claim 1, wherein said pressing step is performed by a press comprising an upper press incorporating the first tool and a lower press incorporating the second tool.

5. A method as set forth in claim 1, wherein said pressing step is performed by a pair of belts comprising an upper belt incorporating the first tool and a lower belt incorporating the second tool.

6. A method as set forth in claim 1, wherein the first tool is made of a thermoplastic, a thermoset polymer material, glass, or quartz.

7. A method as set forth in claim 1, wherein the sheet material includes a dopant that increases radiant absorptivity.

8. A method as set forth in claim 7, wherein the first tool is made of a thermoplastic, a thermoset polymer material, glass, or quartz.

9. A method as set forth in claim 1, wherein the second tool is made of a thermoplastic, a thermoset polymer material, glass, or quartz.

10. A method as set forth in claim 1, wherein the first tool comprises a plurality of recesses, and wherein the second tool comprises a plurality of projections, whereby said pressing steps and said radiant heating steps result in a microneedle array structure comprising a plurality of simultaneously formed microneedles.

11. A method as set forth in claim 1, wherein the recess in the first tool and the projection in the second tool are sized and shaped so that the passageway will extend through the tip of the protrusion.

12. A method as set forth in claim 1, wherein the recess in the first tool and the projection in the second tool are sized and shaped so that the passageway is centrally located in the protrusion.

13. A method as set forth in claim 1, wherein the recess in the first tool and the projection in the second tool are sized and shaped so that the passageway does not extend through the tip of the protrusion.

14. A method as set forth in claim 1, wherein the first tool also has a projection to form an indent surrounding the protrusion.

15. A method of making a microstructure having a protrusion and a passageway extending through the protrusion, said method comprising the steps of:

pressing an embossable sheet material that is one of radiantly transparent or radiantly absorptive between a first tool having a recess which defines the protrusion and a second tool wherein the second tool can be radiantly-transparent or radiantly-absorptive having a projection which defines the passageway; and radiantly heating the sheet material by using radiant energy from a vertically movable radiant energy source by heaters disposed above the first tool and below the second tool;

wherein the first tool is radiantly-transparent and the radiant energy passes therethrough to the sheet material; and wherein at least one of the sheet material and the second tool is radiantly-absorptive.

16. A method as set forth in claim 15, wherein the sheet material is radiantly-transparent and the second tool is radiantly-absorptive.

17. A method as set forth in claim 15, wherein the sheet material is radiantly-absorptive.

\* \* \* \* \*